United States Patent [19]

Tsuda et al.

[11] Patent Number: Plant 6,914

[45] Date of Patent: Jul. 11, 1989

[54] PETUNIA PLANT 'REVOLUTION BRILLIANTPINK'

[75] Inventors: Shinzo Tsuda; Hiroshi Hirabayashi, both of Yachiyo, Japan

[73] Assignees: Suntory Limited, Osaka; Keisei Rose Nurseries, Inc., Tokyo, both of Japan

[21] Appl. No.: 178,416

[22] Filed: Apr. 6, 1988

[30] Foreign Application Priority Data

Oct. 1, 1987 [JP] Japan ..... 62-2480

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Armstrong, Nikaido, Marmelstein, Kubovcik & Murray

[57] ABSTRACT

Disclosed herein is a decumbent type petunia plant having long stems. The plant has abundant branching and a great profusion of blooms, and the whole bush remains in bloom for a considerable period of time. The flowers are single and large and the petals have a metallic luster and a vivid purplish red color with deep reddish purple lines radiating from a dark purple center portion. The plant is highly resistant to rain, heat, and drought.

4 Drawing Sheets

BACKGROUND OF THE VARIETY

The present invention relates to a new and distinct variety of petunia plant obtained from crossing 'Recoverer Scarletred (♀)' and a wild type of petunia plant (♂) native to Brazil.

Petunia is a very popular plant and is used for flower bedding and potting in the summer season. There are only a few varieties of the petunia plant which do not have an upright growth habit and which have a high resistance to rain, heat, and drought. Accordingly, this invention was aimed at obtaining a new variety of decumbent habit petunia plant having long stems and large blooms, the bush remaining in bloom for a considerable period of time, and a high resistance to rain, heat, and drought.

The new variety of petunia plant according to this invention originated from a crossing of 'Recoverer Scarletred' as the female parent and a wild type of petunia plant native to Brazil as the pollen parent, in June, 1984 at the Yachiyo Farm of Keisei Rose Nurseries, Inc., residing at 755 Ōwadasinden, Yachiyo-shi, Chiba-ken, Japan. From this crossing 380 seedlings were obtained in 1985, from which 3 seedlings were selected, propagated by cutting, and then grown as a trail by flower bedding. Only one of the 3 resulting plants was selected. The botanical characteristics of the finally-selected plant were then examined, using a similar variety, 'Recoverer Blue', for comparison, from the spring of 1986. As a result, it was concluded that this petunia plant is distinguishable from any other variety, whose existence is known to us, and this new variety of petunia plant was named 'Revolution Brilliantpink'.

In the following description, the color-coding is in accordance with the Horticultural Colour Chart of The Royal Horticultural Society, London, England (R.H.S. Colour Chart), and the Inter-Society Color Council-Nation Bureau of Standards Color Name (I.S.C.C.-N.B.S. Color Name). A color chart based on The Japan Color Standard for Horticultural Plant (J.H.S. Color Chart) is also added for reference.

'Recoverer Scarletred', also called 'Recoverer Scarlet' or 'Recoverer Red', used as the female parent in the breeding of this new variety 'Revolution Brilliantpink', is one of the Recoverer Series bred by the Sakata Seed Corp., Japan. The Recoverer Series includes the above-mentioned 'Recoverer Blue' used as a comparative variety in the examination, 'Recoverer White', and 'Recoverer Pink', and these plants are commonly characterized by a high resistance to rain. The main botanical characteristics of 'Recoverer Scarletred' are as follows.

Plant:

*Growth habit.*—Upright.

*Plant height.*—30–40 cm.

*Spreading area of plant.*—25–35 cm in diameter.

*Blooming period.*—April to September in the southern Kantō area, Japan.

Stem:

*Thickness.*—Main stem 4.5–6.5 mm; lateral stem 2.0–3.0 mm.

*Color.*—Strong yellow green (R.H.S. 144B–144C, J.H.S. 3512–3513).

*Branching.*—Abundant.

*Pubescence.*—Normal.

*Length of internode.*—2.0–3.0 cm before blooming; 2.0–4.0 mm during blooming.

Leaf:

*Phyllotaxis.*—Verticillate before blooming; opposite during blooming.

*Shape.*—Lancet.

*Size (average).*-4.0–5.0 cm×2.0–3.5 cm.

*Thickness.*—0.4–0.6 mm.

*Color.*—Strong yellow green to moderate olive green (R.H.S. 144A–146A, J.H.S. 3507–3508).

*Pubescence.*—Few.

Flower: Opening obliquely upward.

*Type.*—Single.

*Shape.*—Funnel-shape, with five-fissured limb.

*Diameter.*—8.0–8.5 cm.

*Color.*—When flower is open, bright red (R.H.S. 45C–47B, J.H.S. 0407), with moderate pink (R.H.S. 51C–54C, J.H.S. 0113) reverse side.

*Reproductive organs.*—1 pistil and 5 stamens, both normal.

*Peduncle.*—1.5–2.5 mm in thickness, and 2.5–3.0 cm in length.

Physiological and ecological characteristics: High resistance to rain, heat, and disease, and moderate resistance to pest.

The male parent used in the breeding of 'Revolution Brilliantpink' is a wild type of petunia native to Brazil, the seeds of which were gathered at Gramado, Rio Grande Do Sul, Brazil and introduced to Japan in October, 1983. This wild type of plant is presently maintained at the aforementioned Yachiyo Farm of the Keisei Rose Nurseries, Inc. The main botanical characteristics of this male parent are as follows.

Plant:

*Growth habit.*—Decumbent.

*Plant height.*—20 cm.

*Spreading area of plant.*—100–150 cm in diameter.

*Blooming period.*—May to August in the southern Kantō area, Japan.

Stem:

*Length from base.*—50–80 cm.

*Thickness.*—Main stem 2.0–3.0 mm; lateral stem 1.5–2.5 mm.

*Color.*—Strong yellow green (R.H.S. 144B–144C, J.H.S. 3512–3513).

*Branching.*—Over-abundant.

*Pubescence.*—Many.

*Length of intermode.*—1.0–2.0 cm before blooming; 1.5–3.0 cm during blooming.

Leaf:

*Phyllotaxis.*—Opposite both before and during blooming.

*Shape.*—Oval.

*Size (average).*—4.5–5.5 cm×2.5–3.5 cm.

*Thickness.*—0.4–0.5 mm.

*Color.*—Grayish olive green (R.H.S. 137A–137B, J.H.S. 3716–3717).

*Pubescence.*—Few.

Flower: Opening obliquely upward.

*Type.*—Single.

*Shape.*—Funnel-shape, with five-fissured limb.

*Diameter.*—4.0–5.0 cm.

*Color.*—In the unopened stage (bud), dark reddish purple (R.H.S. 79B, J.H.S. 8907–8909); when open, vivid reddish purple (R.H.S. 74A, J.H.S. 9207); at full bloom, vivid reddish purple (R.H.S. 80A, J.H.S. 8906).

*Reproductive organ.*—1 pistil and 5 stamens, both normal.

*Peduncle.*—0.9–1.2 mm in thickness, and 2.0–2.5 mm in length.

Physiological and ecological characteristics: High resistance to cold, relatively high resistance to heat, and moderate resistance to disease and pest.

This new and distinct variety of petunia plant, 'Revolution Brilliantpink', was asexually reproduced by cutting at the aforementioned Yachiyo Farm of Keisei Rose Nurseries, Inc., and the homogeneity and stability thereof were confirmed.

SUMMARY OF THE VARIETY

The new variety of petunia plant has a decumbent habit and long stems, and thus is very different from a similar variety, 'Recoverer Blue', having an upright growth habit. The plant has abundant branching and a great profusion of blooms, and the whole bush remains in bloom for a considerable period of time, longer than the bloom period of 'Recoverer Blue'. The flowers are single, and large, but somewhat smaller than 'Recoverer Blue', and the petals have a metallic luster and a vivid purplish red color, which is lighter than the deep purple of 'Recoverer Blue', with deep reddish purple lines radiating from a dark purple center portion. The plant is highly resistant to rain, heat, and drought.

The following Table shows the main distinguishable features of this variety 'Revolution Brilliantpink' in comparison with the similar variety 'Recoverer Blue'.

TABLE

Main distinguishing features of 'REVOLUTION BRILLIANTPINK' compared with 'Recoverer Blue'.

| Characteristics | 'REVOLUTION BRILLIANTPINK' | 'Recoverer Blue' |
|---|---|---|
| 1. Growth habit | Decumbent | Upright |
| 2. Stem length from base | 50–80 cm | 30–40 cm |
| 3. Blooming period (in the southern Kanto area, Japan) | Late March to late September | April to September |
| 4. Diameter of flower | 7.0–8.0 cm | 8.0–8.5 cm |
| 5. Color of flower at full bloom | Vivid purplish red (RHS 74A, JHS 9507-9207) | Deep purple (RHS 83A, JHS 8606-8609) |

DESCRIPTION OF THE VARIETY

Figure 1:
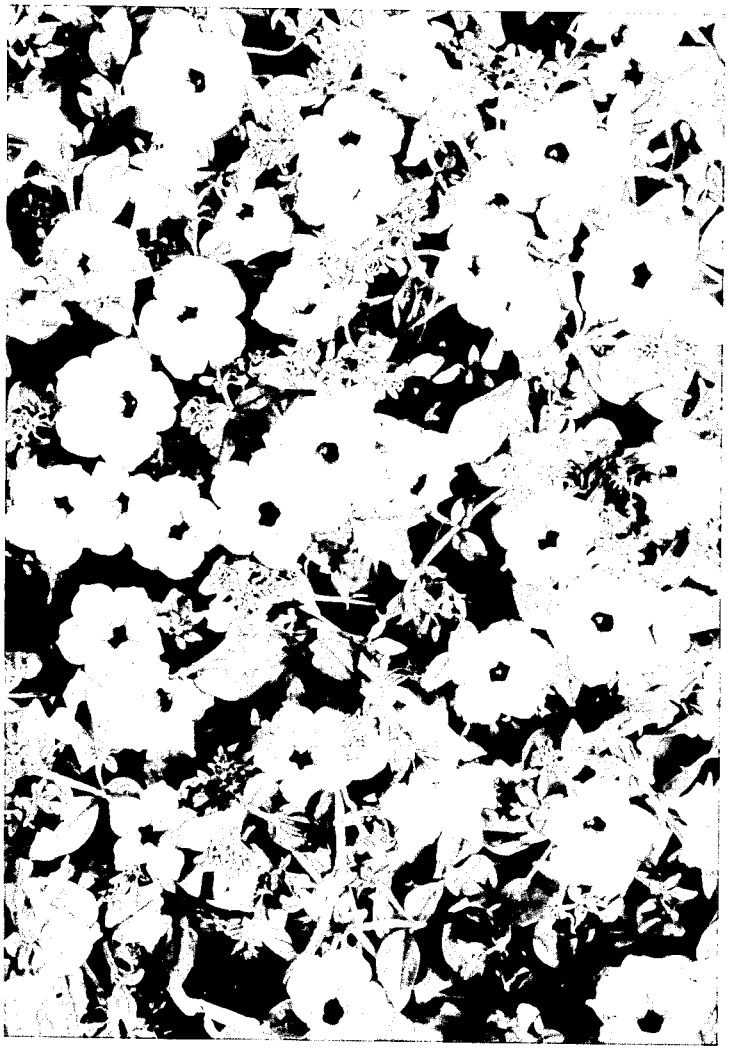
FIG. 1 is a photograph giving a partial view of the new variety of petunia plant planted in a flower bed.
Figure 2:
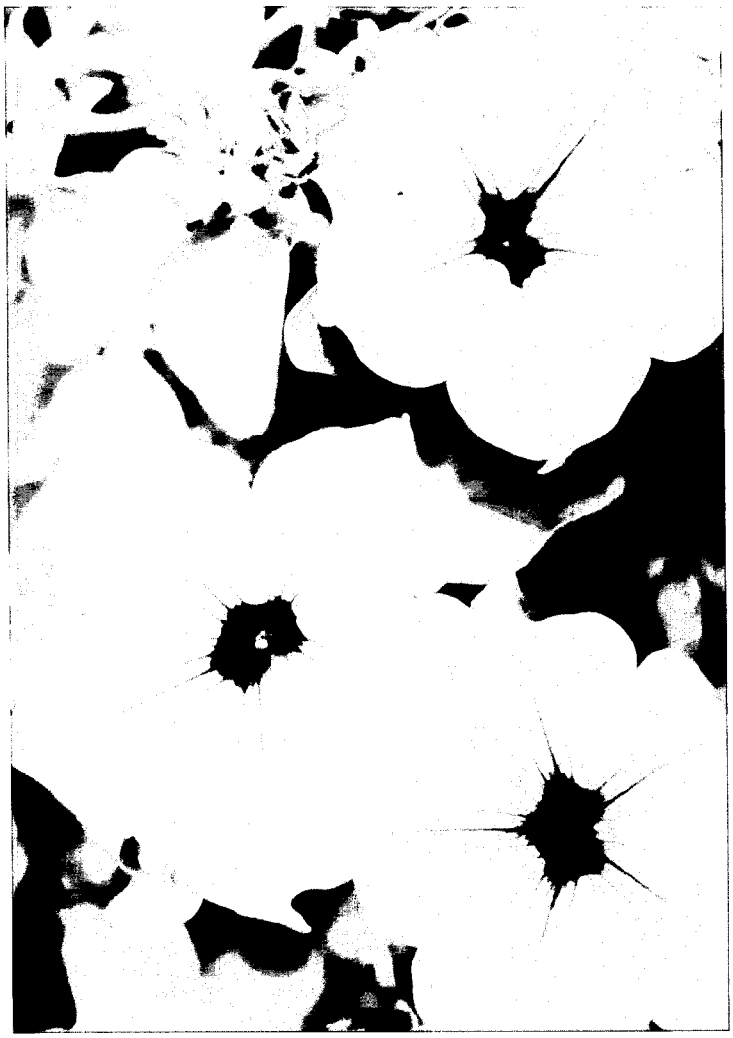
FIG. 2 is a photograph of flowers of the new variety of petunia plant.
Figure 3:
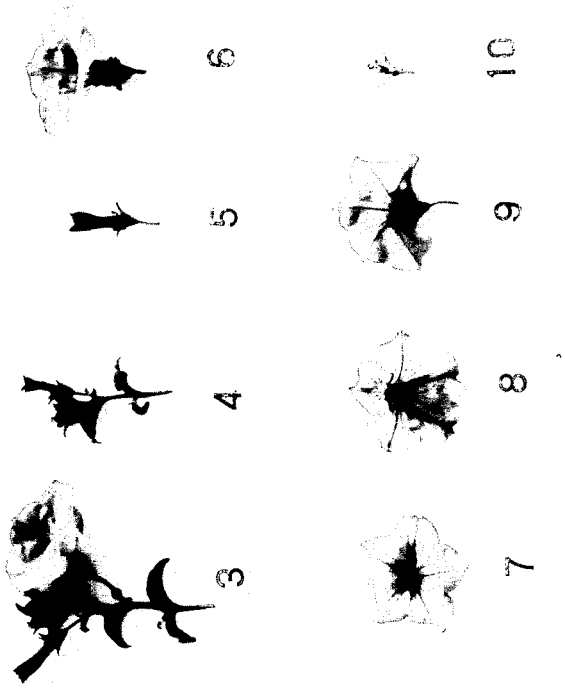
FIG. 3 is a photograph showing, in numerical order, a branch having an open flower (3), a current shoot (4), a bud (5), a side view of the flower (6), a front view of the flower (7), a rear view of the flower (8), an interior view of the flower (9), and pistil and stamens (10), of the new variety of petunia plant; and, FIG. 4 is a photograph showing, in numerical order, a branch having an open flower (1), a flower (2), a bud (3), and a current shoot (4) of the new variety of petunia plant, in comparison with corresponding items (5–8) of a similar variety 'Recoverer Blue'.
Figure 4:
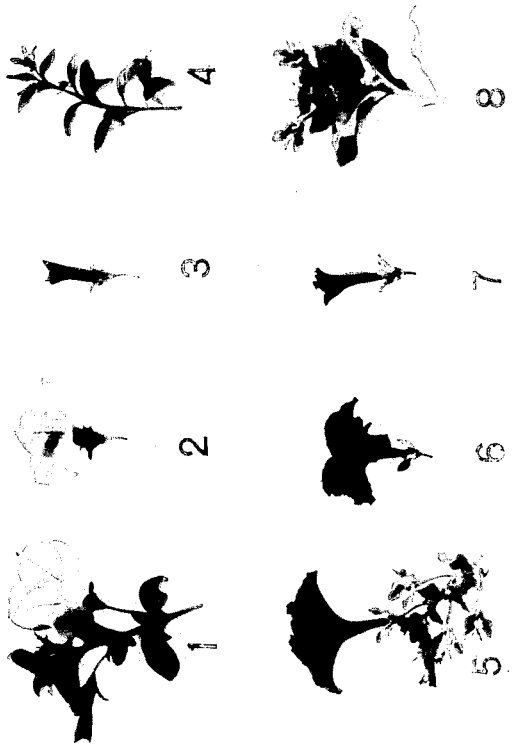

The botanical characteristics of the new and distinct variety of petunia plant 'Revolution Brilliantpink' are as follows.

Plant:

*Growth babit.*—Decumbent. The stem hang down where potted in a hanging pot.

*Plant height.*—15–20 cm.

*Spreading area of plant.*—The stem extends to a length of 50–80 cm from the base, and thus the spreading area of the plant is 100–150 cm in diameter.

*Growth.*—Very vigorous with abundant branching, a great profusion of blooms; the whole bush remaining in bloom for a considerable period of time.

*Blooming period.*—Late March to late September, in the southern Kantō area, Japan. The plant shape does not change throughout this period.

Stem:

*Thickness.*—Main stem 2.5–3.5 mm; lateral stem 1.5–2.0 mm.

*Color.*—Strong yellow green (R.H.S. 144A–145A, J.H.S. 3507–3712).

*Pubescence.*—Normal.

*Branching.*—Over-abundant.

*Length of internode.*—1.5–1.7 cm before blooming; 3.0–4.0 cm during blooming.

Leaf:

*Phyllotaxis.*—Verticillate before blooming; opposite during blooming.

*Shape.*—Lancet.

*Size (average).*—6.0–7.0 cm×2.5–3.5 cm.

*Thickness.*—0.6–0.8 mm.

*Color.*—Moderate olive green to strong yellow green (R.H.S. 146A–143A, J.H.S. 3508–3308).

*Pubescence.*—Few.

Flower: Opening obliquely upward.

*Type.*—Single.

*Shape.*—Funnel-shape, with five-fissured limb.

*Diameter.*—7.0–8.0 cm, large.

*Color.*—In the unopened stage (bud), dark reddish purple (R.H.S. 79A–79B, J.H.S. 9516–9210); when open, dark purplish red (R.H.S. 71A, J.H.S. 9509); at full bloom, vivid purplish red (R.H.S. 74A, J.H.S. 9507–9207), with deep reddish purple (R.H.S. 77A, J.H.S. 9209–9210) lines radiating from a dark purple (R.H.S. 83A, J.H.S. 8609–8610) center portion. The reverse side of the petal is a vivid reddish purple color (R.H.S. 74A, J.H.S. 9208–9206). The petal has a metallic luster.

*Reproductive organs.*—1 normal pistil having a grayish olive green (R.H.S. 137A, J.H.S. 3716) stigma, and 5 normal stamens each having a deep purple (R.H.S. 86A, J.H.S. 8307) anther and a light purple (R.H.S. 87D, J.H.S. 8603) filament.

*Peduncle.*—1.5–2.0 mm in thickness, and 1.5–2.0 cm in length.

Physiological and ecological characteristics: High resistance to rain, heat, and drought. Also high resistance to disease, particularly gray mold (Botrytis). Moderate resistance to pest.

This new variety of petunia plant is most suitable for flower bedding and potting, particularly in hanging pots or planters, and further excellent for ground cover.

The plant of this new variety 'Revolution Brilliant-pink' is presently planted and maintained at the Yachiyo Farm of the Keisei Rose Nurseries, Inc., residing at 755 Ōwadasinden, Yachiyo-shi, Chiba-ken, Japan.

We claim:

1. A new and distinct variety of petunia plant, substantially as herein illustrated and described, characterized particularly as to novelty by (A) being a decumbent habit plant having long stems, (B) an abundant branching and a great profusion of blooms, the whole bush remaining in bloom for a considerable period of time, (C) flowers that are single and large, the petals having a metallic luster and a vivid purplish red color with deep reddish purple lines radiating from a dark purple center portion, and (D) a high resistance to rain, heat, and drought.

* * * * *